US006818602B2

(12) United States Patent
Haag

(10) Patent No.: US 6,818,602 B2
(45) Date of Patent: Nov. 16, 2004

(54) SOAP SYSTEM COMPRISING DIRT SCENT

(76) Inventor: Kathy J. Haag, 7461 62nd. Ave. SE., Fredonia, ND (US) 58440

( * ) Notice: Subject to any disclaimer, the term of this patent is extended or adjusted under 35 U.S.C. 154(b) by 67 days.

(21) Appl. No.: 10/307,009

(22) Filed: Nov. 27, 2002

(65) Prior Publication Data

US 2004/0102342 A1 May 27, 2004

(51) Int. Cl.[7] .................................................. A61K 7/50

(52) U.S. Cl. ........................ 510/101; 510/140; 510/141; 510/152; 510/439

(58) Field of Search ................................. 510/141, 152, 510/140, 439, 101

(56) References Cited

U.S. PATENT DOCUMENTS 4,077,754 A * 3/1978 Borcher et al. .......... 425/131.1
4,191,660 A * 3/1980 Schreiber et al. ........... 510/105
6,242,397 B1 * 6/2001 Milio et al. ................. 510/140

* cited by examiner

*Primary Examiner*—Necholus Ogden

(57) ABSTRACT

A soap system for efficiently cleaning a hunter and covering their human scent with an earthy scent. The soap system includes heating a volume of soap to a melting point and then mixing a dirt scent into the melted soap. The mixture is then poured into a mold, hardened, removed and then cut into a plurality of bar members. The bar members are then wrapped with an inner covering and an outer covering. The inner covering is preferably comprised of a non-permeable material. The outer covering is preferably comprised of a camouflage material and design.

18 Claims, 6 Drawing Sheets

SOAP SYSTEM COMPRISING DIRT SCENT

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to soap and more specifically it relates to a soap system for efficiently cleaning a hunter and covering their human scent with an earthy scent.

2. Description of the Related Art

Soap has been in use for years. Soap is typically comprised of either liquid soap or solid bar soap. The main problem with conventional soap is that the user is left with a residue smell of the soap which can be detected by wild animals. Many hunters will avoid utilizing soap for a period of days in an attempt to avoid being "contaminated" with the smell of soap.

While these products may be suitable for the particular purpose to which they address, they are not as suitable for efficiently applying an earthy scent to an individual. Conventional soap does not cover up the human scent and conventional scent cover up solutions do not cleanse an individual.

In these respects, the soap system according to the present invention substantially departs from the conventional concepts and designs of the prior art, and in so doing provides a system primarily developed for the purpose of efficiently applying an earthy scent to an individual.

BRIEF SUMMARY OF THE INVENTION

In view of the foregoing disadvantages inherent in the known types of soap now present in the prior art, the present invention provides a new soap system construction wherein the same can be utilized for efficiently applying an earthy scent to an individual.

The general purpose of the present invention, which will be described subsequently in greater detail, is to provide a new soap system that has many of the advantages of the soap mentioned heretofore and many novel features that result in a new soap system which is not anticipated, rendered obvious, suggested, or even implied by any of the prior art soap, either alone or in any combination thereof.

To attain this, the present invention generally comprises heating a volume of soap to a melting point and then mixing a dirt scent into the melted soap. The mixture is then poured into a mold, hardened, removed and then cut into a plurality of bar members. The bar members are then wrapped with an inner covering and an outer covering. The inner covering is preferably comprised of a non-permeable material. The outer covering is preferably comprised of a camouflage material and design.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a soap system that will overcome the shortcomings of the prior art devices.

A second object is to provide a soap system for efficiently applying an earthy dirt scent to an individual.

Another object is to provide a soap system that may be utilized in various situations such as during a shower or in the field.

An additional object is to provide a soap system that covers the human scent of an individual to avoid wild game from smelling their scent.

A further object is to provide a soap system that simultaneously cleans a hunter and covers the human scent.

Another object is to provide a soap system that allows hunters to approach wild game in a close manner without detection.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
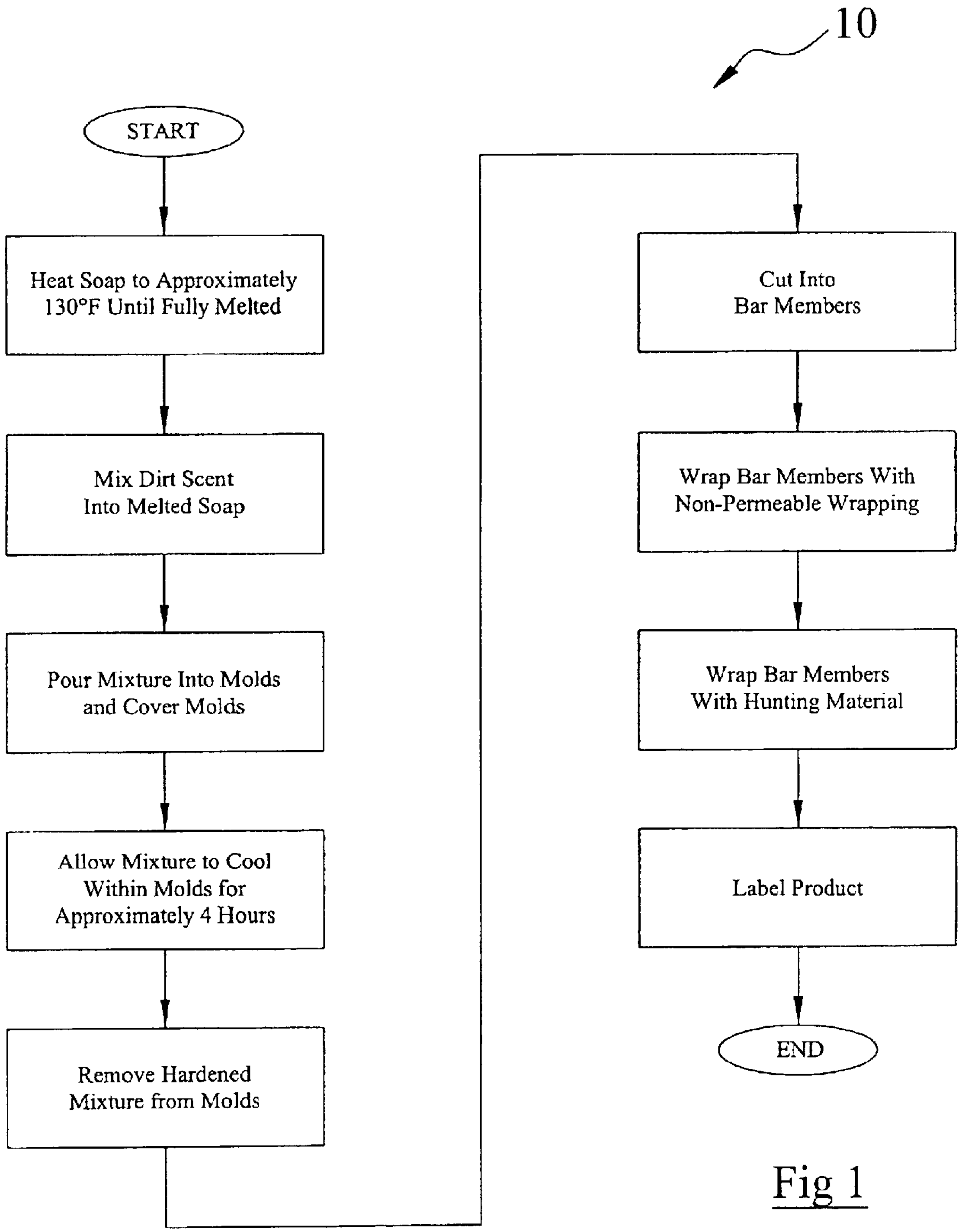
FIG. 1 is a flowchart illustrating the manufacture of the present invention
Figure 2:
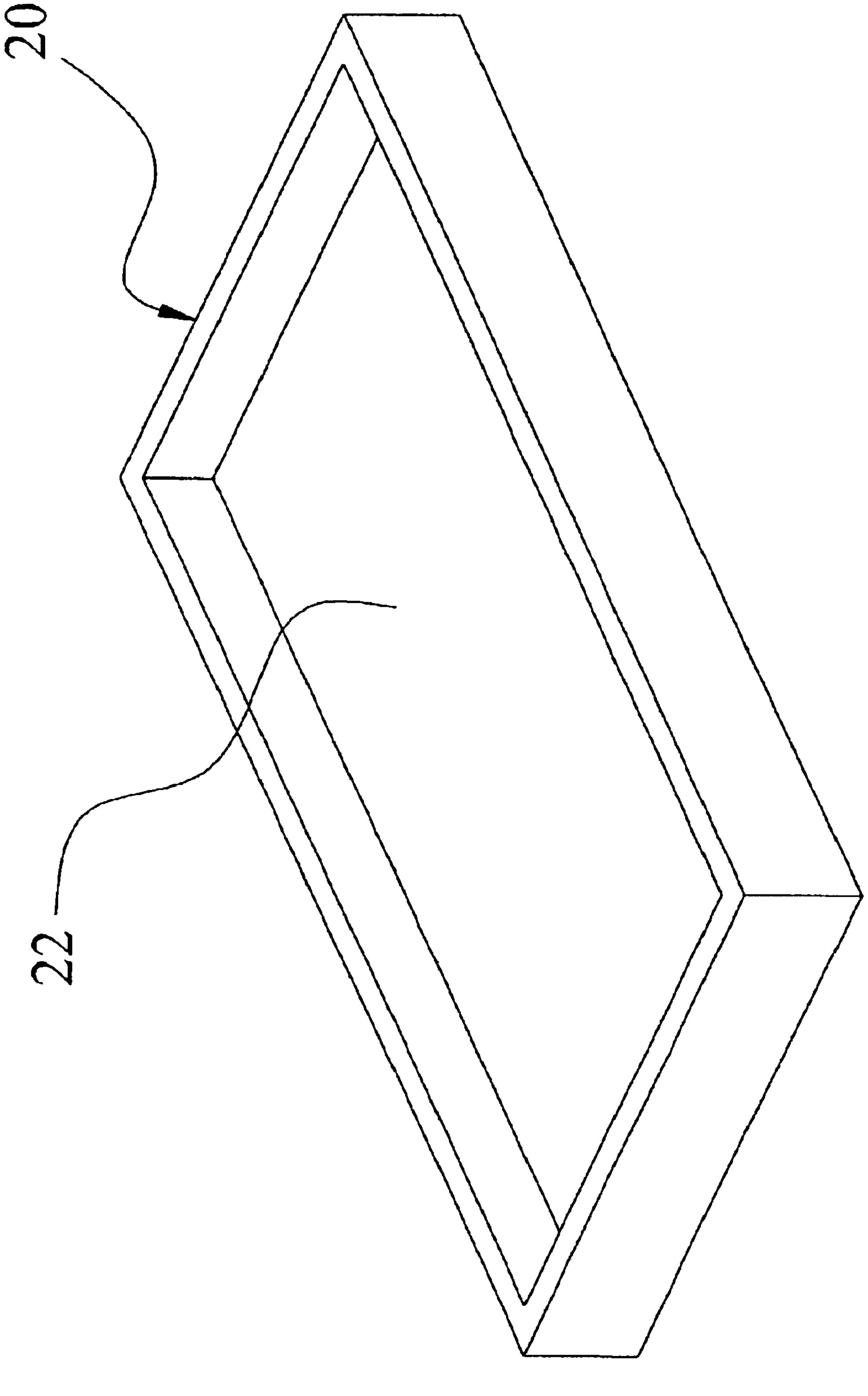
FIG. 2 is an upper perspective view of an exemplary mold utilized to manufacture the block member.

Turning now descriptively to the drawings, in which similar reference characters denote similar elements throughout the several views, FIGS. 1 through 6 illustrate a soap system 10, which comprises heating a volume of soap to a melting point and then mixing a dirt scent into the melted soap. The mixture is then poured into a mold 20, hardened, removed and then cut into a plurality of bar members 40. The bar members 40 are then wrapped with an inner covering 50 and an outer covering 60. The inner covering 50 is preferably comprised of a non-permeable material. The outer covering 60 is preferably comprised of a camouflage material and design.

The soap utilized preferably is unscented with no performs and limited odor. The soap may or may not have pumice within for enhancing the cleaning of an individual. The soap may be transparent, translucent or colored.

The soap is preferably comprised of a glycerin soap base which is commercially available throughout the soap industry. There are various potential glycerin soap bases that may be utilized.

For example, the ingredients of the glycerin soap base may be comprised of various volumes of the following ingredients: coconut oil, palm oil, castor oil, safflower oil, glycerin, water, sodium hydroxide, sorbitol, sorbitan oleate and soybean protein. The applicant has found this composition to provide the desired formulation for the soap base.

The first step in the manufacturing process is to melt the soap by heating the soap to a temperature of approximately 130 degrees Fahrenheit. After the soap is fully or partially melted, the user then inputs a volume of earthy dirt scent into the melted soap and thoroughly mixes the dirt scent into the melted soap. The dirt scent preferably has an earthy smell similar to the scent of dirt which facilitates covering up the user's human scent.

The dirt scent may be comprised of a liquid, gel or powder base. The preferred dirt scent utilized is sold by WHOLESALESUPPLIESPLUS.COM, INC. (www.wholesalesuppliesplus.com) under the brand name DIRT 141. The applicant has found this dirt scent to provide the preferred scent in combination with the soap, however various other dirt and earth scents may be utilized. The applicant has found it desirable to mix approximately two tablespoons of dirt scent with approximately twenty pounds of soap. Various other formulations may be utilized with the present invention.

Figure 3:
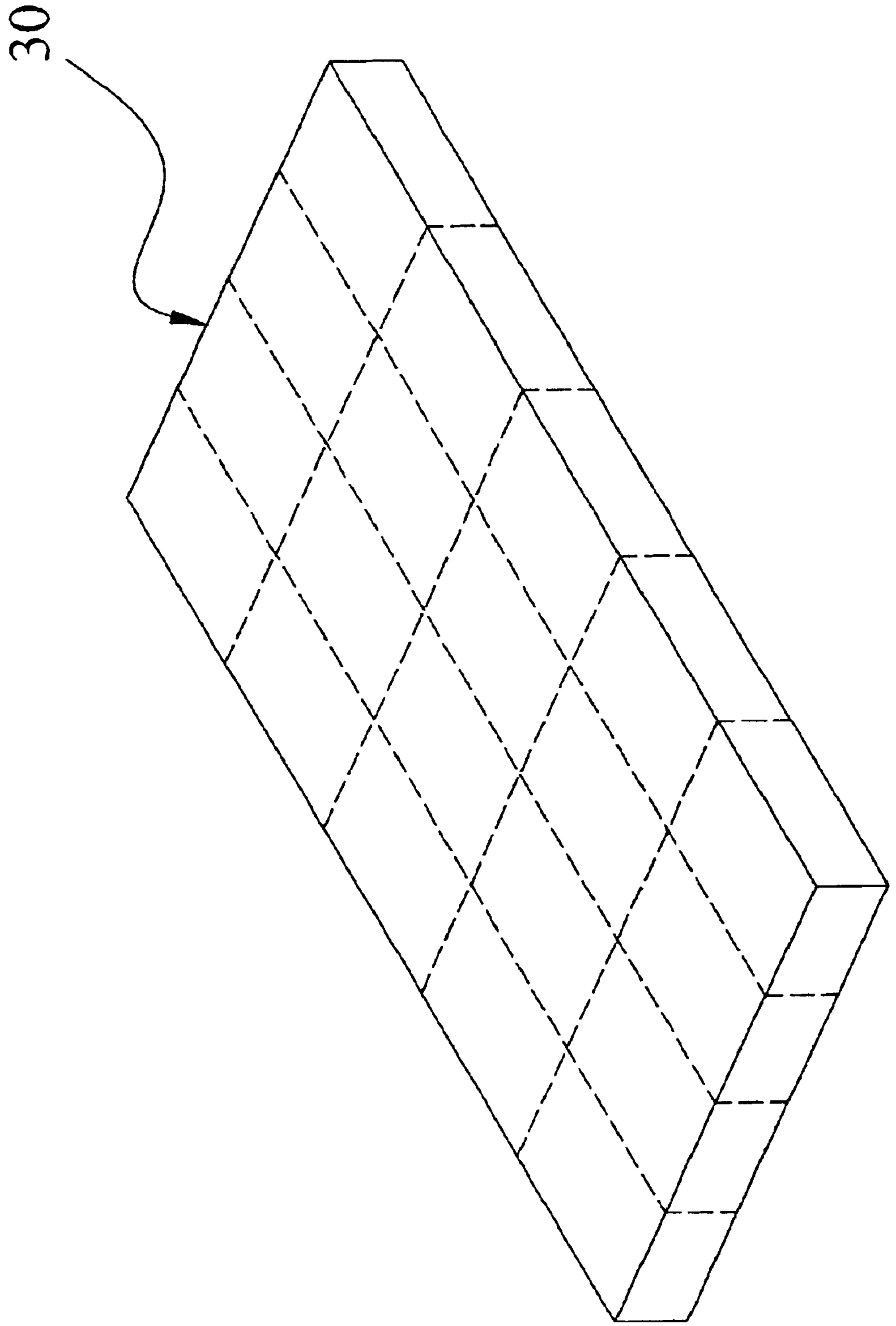
FIG. 3 is an upper perspective view of a solid block member with dashed lines illustrating the locations for cutting the block member.

After the dirt scent is thoroughly mixed with the soap, the combined mixture is then poured into an interior portion 22 of a mold 20 having a desired shape. The mixture is allowed to harden within the mold 20 for approximately three to five hours. After the mixture has hardened, the user then removes the block member 30 from the mold 20 as shown in FIG. 3 of the drawings.

Figure 4:
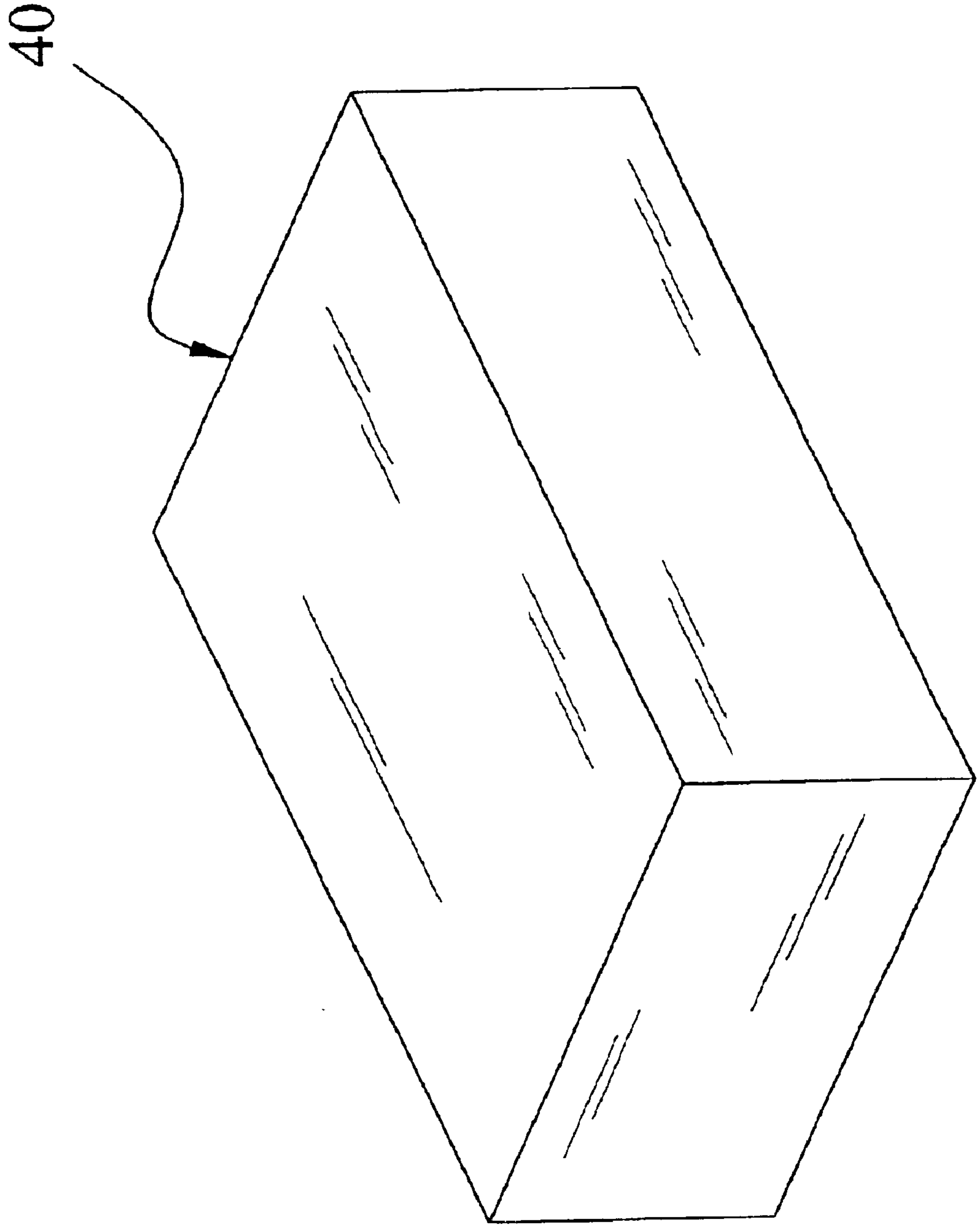
FIG. 4 is a bar member resulting from the cutting of the block member.

The block member 30 is then cut into smaller bar members 40 as shown in FIG. 4 of the drawings. The bar members 40 may be further shaped or left as a rectangular structure as shown in FIG. 4 of the drawings. The bar members 40 may have various shapes and sizes as desired.

After the bar member 40 is formed, it is preferably to immediately wrap and seal the bar member 40 with an inner covering 50 to prevent loss of the dirt scent and exposure to air. The inner covering 50 is preferably comprised of a non-permeable flexible material such as but not limited to plastic and other common packaging materials.

Figure 5:
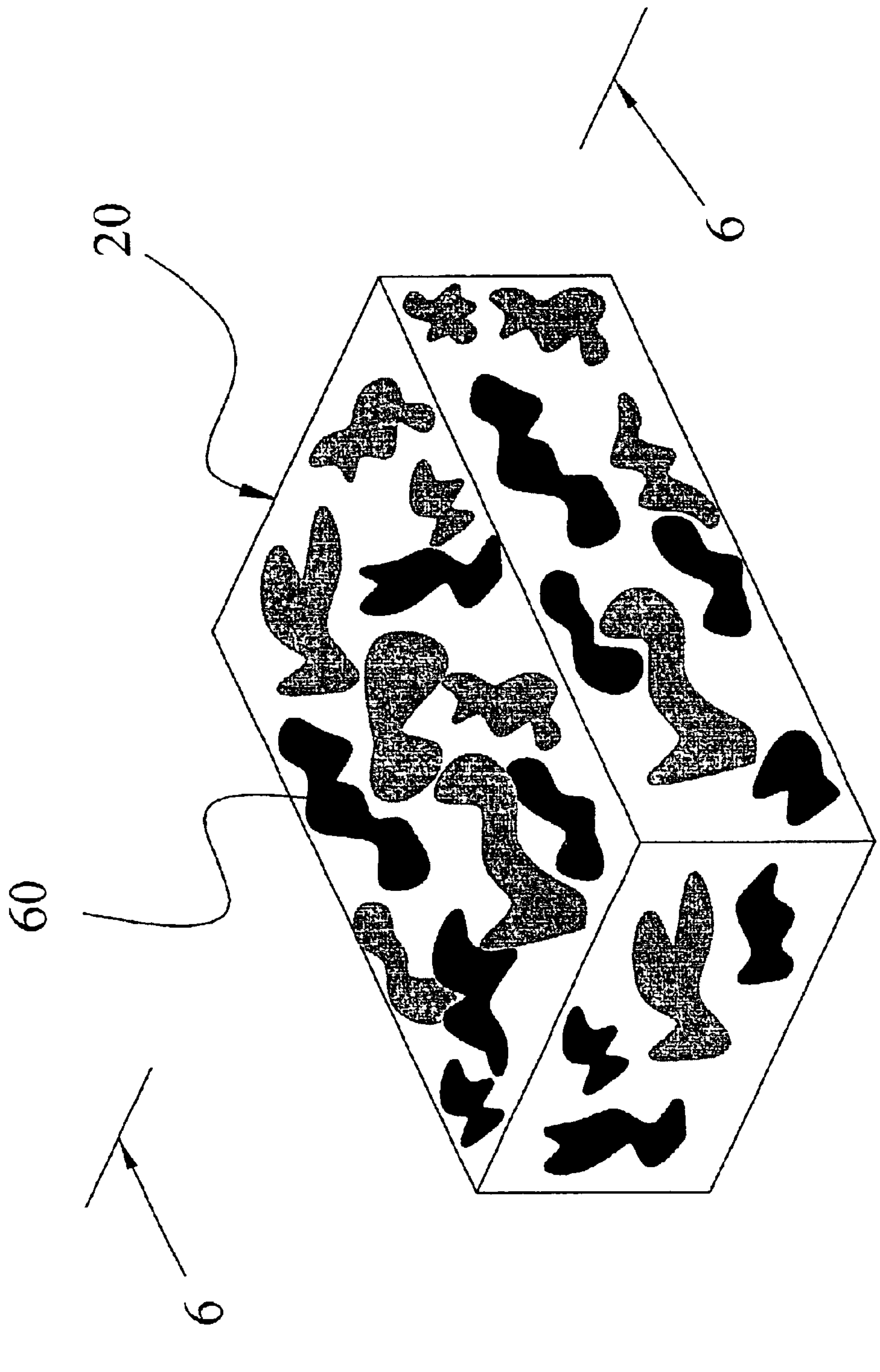
FIG. 5 is an upper perspective view of a block member surrounding by an inner covering and an outer covering.
Figure 6:
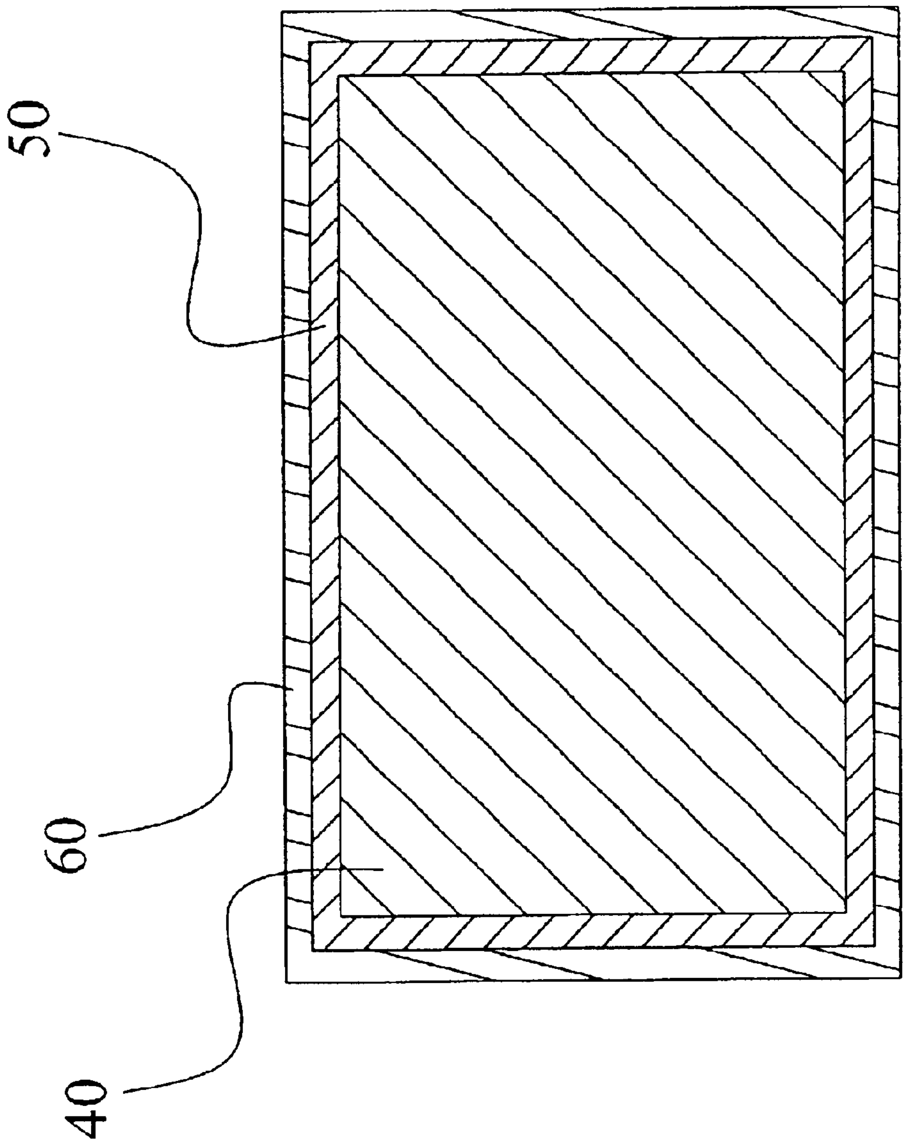
FIG. 6 is a cross sectional view taken along line 6—6 of FIG. 5.

Once the bar member 40 is properly sealed with the inner covering 50, it is desirable to add an outer covering 60 about the bar member 40 which has a camouflage design as shown in FIGS. 5 and 6 of the drawings. The camouflage design may have various designs and colors which are commonly utilized within the camouflage industry. The outer covering 60 is preferably comprised of a cloth material commonly utilized within the camouflage industry, however other non-cloth materials may be utilized to construct the outer covering 60. A label may be secured onto an upper surface or about the entire bar member 40 prior to transporting to a store or consumers.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed to be within the expertise of those skilled in the art, and all equivalent structural variations and relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A bar soap member, comprising:

a volume of soap comprised of the following ingredients: coconut oil, palm oil, castor oil, safflower oil, glycerin, water, sodium hydroxide, sorbitol, sorbitan oleate and soybean protein; and a volume of dirt scent contained within said volume of soap.

2. The bar soap member of claim 1, wherein said volume of dirt scent is less than 5% of said volume of soap.

3. The bar soap member of claim 1, wherein said dirt scent has an earthy scent.

4. The bar soap member of claim 1, wherein said dirt scent has a muddy scent.

5. The bar soap member of claim 1, wherein said volume of dirt scent is less than 2% of said volume of soap.

6. The bar soap member of claim 1, wherein said volume of dirt scent is less than 1% of said volume of soap.

7. The bar soap member of claim 1, wherein said volume of soap is comprised of a glycerin soap base.

8. The bar soap member of claim 1, wherein said volume of soap and said volume of dirt scent are formed into a rigid solid structure.

9. The bar soap member of claim 8, wherein said rigid solid structure has a rectangular shape.

10. The bar soap member, comprising:

a volume of soap comprised of the following ingredients: coconut oil, palm oil, castor oil, safflower oil, glycerin, water, sodium hydroxide, sorbitol, sorbitan oleate and soybean protein;

a volume of dirt scent contained within said volume of soap;

an inner covering surrounding said bar soap member, wherein said inner covering is non-permeable; and an outer covering surrounding said inner covering, wherein said outer covering has a camouflage design.

11. The bar soap member of claim 10, wherein said outer covering is comprised of a cloth material.

12. The bar soap member of claim 10, wherein said dirt scent has an earthy scent.

13. The bar soap member of claim 10, wherein said dirt scent has a muddy scent.

14. The bar soap member of claim 10, wherein said volume of dirt scent is less than 2% of said volume of soap.

15. The bar soap member of claim 10, wherein said volume of dirt scent is less than 1% of said volume of soap.

16. The bar soap member of claim 10, wherein said volume of soap is comprised of a glycerin soap base.

17. A method of manufacturing a bar soap product having an earthy scent, said method comprising:

providing a volume of soap comprised of the following ingredients: coconut oil, palm oil, castor oil, safflower oil, glycerin, water, sodium hydroxide, sorbitol, sorbitan oleate and soybean protein;

heating said soap until fully melted;

adding a volume of dirt scent to said soap forming a scented soap mixture;

pouring said scented soap mixture into an interior of a mold;

allowing said scented soap mixture to harden;

removing said scented soap mixture from said mold in a hardened state; and cutting said scented soap mixture into a plurality of bar members.

18. The method of manufacturing a bar soap product having an earthy scent of claim 17, including the steps of:

surrounding said bar members with an inner covering, wherein said inner covering is comprised of a non-permeable material; and surrounding said inner covering with an outer covering, wherein said outer covering has a camouflage design.

* * * * *